(12) United States Patent
Himes

(10) Patent No.: US 6,793,881 B2
(45) Date of Patent: Sep. 21, 2004

(54) CONTAINER AND METHOD FOR CONDITIONING ARTICLES OF HUNTING CLOTHING AND RELATED GEAR

(76) Inventor: Wayne Himes, 229 Southwest Rd., Canterbury, NH (US) 03224

(*) Notice: Subject to any disclaimer, the term of this patent is extended or adjusted under 35 U.S.C. 154(b) by 291 days.

(21) Appl. No.: 09/924,132

(22) Filed: Aug. 8, 2001

(65) Prior Publication Data
US 2003/0031582 A1 Feb. 13, 2003

(51) Int. Cl.[7] .............................................. A61L 9/01
(52) U.S. Cl. ........................ 422/5; 422/1; 422/292; 422/297; 34/104; 34/202; 34/218
(58) Field of Search ........................ 422/1, 5, 292, 422/297; 34/104, 202, 218; 190/19, 13 R, 24; 239/36, 57

(56) References Cited

U.S. PATENT DOCUMENTS

| | | | | |
|---|---|---|---|---|
| 4,854,501 A | * | 8/1989 | Ricci ............................ | 239/54 |
| 5,165,181 A | * | 11/1992 | Acosta et al. ................ | 34/90 |
| 5,592,750 A | * | 1/1997 | Eichten ........................ | 34/104 |
| 5,776,378 A | * | 7/1998 | Knight ........................ | 261/30 |
| 6,062,416 A | * | 5/2000 | Smillie ........................ | 220/524 |
| 6,263,591 B1 | * | 7/2001 | La Porte ...................... | 34/622 |
| 2003/0012680 A1 | * | 1/2003 | Balsys .......................... | 422/5 |
| 2003/0015513 A1 | * | 1/2003 | Ellis ............................ | 219/400 |

* cited by examiner

Primary Examiner—Robert J. Warden, Sr.
Assistant Examiner—Sean E. Conley
(74) Attorney, Agent, or Firm—Donald Grant Kelly

(57) ABSTRACT

A container and method for conditioning articles of hunting clothing and related gear so as to camouflage scents associated with humans. The container presents an enclosed space with an easily accessible opening where clothing and other gear may be placed. Within the confines of the container, one or more internal compartments are formed to hold natural, woodsy materials pre-selected as a natural scent source. Each internal compartment is provided passages permitting permeation of scents into the space where the clothing and gear are located, while preventing soiling contact with the scent source materials and the clothing articles. Each compartment includes a hinged portion such that source material may be changed or refreshed. Typically, the container is in the form of a transportable trunk with a lid pivoted on a horizontal axis. Scent-source material compartments are formed within and near a bottom surface of the container and within the hinged lid, such that the hunting clothing and gear will be enclosed between the scent source when the container is closed.

22 Claims, 3 Drawing Sheets

CONTAINER AND METHOD FOR CONDITIONING ARTICLES OF HUNTING CLOTHING AND RELATED GEAR

BACKGROUND OF THE INVENTION

1. Field of the Invention

This device and method relates to the field of hunting, and more specifically to the challenge hunters face in avoiding detection by game due to certain scents the hunter may unavoidably or unwittingly carry with them to the hunt. For thousands of years, the hunting of big game has commanded the utmost cleverness on the part of the hunter to avoid detection by highly developed senses of his or her prey.

Complementing their natural fitness, strength, swiftness and instincts, animals enjoy keenly developed senses among their primary protection devices. Besides their exceptional sight and hearing capacities, many say that an animal's most powerfully protective ally lies in its remarkable olfactory sense. Long ago, hunters knew that simply striving to remain downwind of their prey would be insufficient to avoid detection.

This has brought about great numbers of techniques by hunters to remove or obfuscate the odors they bring to the forest. These include artificially developed, odor-hiding sprays applied repeatedly while on the hunt, washing the hunter's garb in unscented detergent, wearing odorless clothing liners that prevent the emanation of scents, and even applying animal lure scents to attract the game to the hunter.

This problem of detection has become exacerbated in more recent times when unnatural chemicals, especially those with the very purpose of creating new odors, have become a large part of the typical hunter's life. Deodorants, breath mints, special coffee blends, car interior scents, shaving lotions, perfumes, toothpaste, hair gels, alcohol, hand lotions, cold medications, fabric softeners, food odors, scented tissues, gasoline and oil traces—the list is endless. Ever day, chemical industries develop still newer scents to add to the mix, and complicate the hunt.

For hundreds of years, hunters have awaited the development of a simple, inexpensive, and easy to use method and device for countering the scent-detection problem.

2. Description of the Related Art

Over the years, many attempts have been set forth to address the problem of human associated scent detection by wild game. Among those many who have recognized the problem is Maples, U.S. Pat. No. 5,024,008, with a rubber overshoe to insulate the odor-emitting boot from contacting the ground. Rubber, however, carries its own human-associated odor. Whitlock, in U.S. Pat. No. 6,202,324 brings an improved form of odorless footwear, but this does nothing to address the more overwhelming problem of general odors emanating from the hunter.

In U.S. Pat. No. 4,722,277, Floyd notes the problems associated with the application of scented oils to the hunters' clothing prior to a hunt, specifically pointing out that the added scent wears out or otherwise dissipates. Floyd addresses this issue through the introduction of scented fabric to be carried by the hunter. This material, while offering more lasting cover for the hunter, requires the hunter to carry more gear, and risks inappropriateness of a pre-selected scent. Besides, this covering-scent approach often leaves the clothes with an unpleasant odor at the conclusion of the hunt.

An invention to remove human associated scents from hunting clothing is set forth by Vickers in U.S. Pat. No. 5,585,107. This requires the acquisition of a sheet of material impregnated with activated carbon to be stored with the clothes overnight. Not all the scents can be removed in this manner, and the typical hunter does not have ready access to the materials needed for the process.

A similar approach, with similar shortcomings, is found in Fore's U.S. Pat. No. 5,891,391, involving the use of a garment bag arrangement holding a granular material which can adsorb the human odor from the clothing. The bag may be tumbled in a clothes dryer, permitting the granular material to be ground into a powder that treats the fabric to take up the human odors. This approach, unfortunately suffers from added complication that the dryer treatment leaves yet another unnatural odor, even if it were to remove all human-emitted odors.

In U.S. Pat. No. 5,899,790, Berg recognizes the need to place scent-source materials, including broken leaf substances that are naturally aromatic, in discrete containers located within a container where clothing to be conditioned is confined. While there are similarities to the approach taken in the subject invention to be disclosed herebelow, the Berg invention itself is wholly inapplicable to the problem at hand. In fact, Berg's invention adds some of the very scents to be avoided in game hunting.

In a device for adding scents to hide human-associated odors, Knight presents an enclosed compartment in which a perforated shelf divides the compartment into upper and lower spaces. Clothing to be conditioned is placed in the upper space. A fan circulates air that picks up an odor from a strategically placed scent cartridge, moving the scented air through the shelf and in contact with the clothing. Supplied with battery power, the device can be used in the field.

The Knight device has definite drawbacks. While the apparatus will impregnate the hunter's clothing with the cartridge-borne scent, it requires substantial mechanical and electrical apparatus to do so. Fan motors carry scents of their own, as do batteries and wiring. Additionally, scents from cartridges, at best, are not natural. They may be inappropriate to the environment of the intended hunt scene. Additionally, they may be emitted under the pressure of other odor-bearing gas. Besides, hunters will surely face discomfort and exposure while conditioning their clothing at the hunt scene.

A similar, though simpler device is shown in the 2001 Cabela's Archery Catalogue. This disclosure, recently published as an advertisement, describes a locker for keeping hunting clothes scent free. Vented compartments of waxed corrugated construction avoid the intrusion of outside odors. A center storage holds leaf bags or scent bars; a waffled bottom elevates clothes to permit scent saturation. This disclosure includes nothing about any internal passages for facilitation of scent transfer. The construction is temporary and not durable, rendering it inadequate to the task at hand. Additionally, the wax substance, cardboard materials and glue carry tell-tail odors of their own, which odors will prove problematic in the field. Finally, with regard to the Cabela disclosure, the invention described more fully herebelow pre-dates this publication, rendering it inapplicable under the terms of Title 35, Section 102 of the United States Code.

Forbes, et al. address the problem of maintaining hunters' clothing scent free during transportation. This invention is to avoid the addition of more scents from such temporary storage media as garbage bag and plastic garment bags.

While, compared to the approach taken by the invention to be described below, Forbes' invention involves adding still more gear to the typical hunt.

These are but a few of the thousands of "solutions" to hunter scent detection problems appearing in the literature as prior art. However, none approaches the problem in the simple, elegant manner described below. And none is as inexpensive, easy to use, portable, and adaptable as the invention claimed herein.

SUMMARY OF THE INVENTION

A clothing conditioning apparatus and method employ a container means, referred to herein by the trademark HUNTER'S TRUNK™ and designed as a box-like structure. An upper hinged lid, a bottom surface and four walls essentially define the container means, in its preferred embodiment. Within discrete chambers of the box-like structure, scent-source materials are confined so as to be adjacent to, but not touching, a hunter's clothing articles and associated gear to be conditioned. In anticipation of a hunting event, the hunter's clothing will be stored in the container means where they will be subjected to odor treatment or preconditioning by the natural scent-source material.

Within the bottom-most space of the container means, a panel means including a plurality of small airflow passages defines a first discrete chamber or compartment means for scent-source storage. At an upper level of the container, within said hinged lid, a second panel means is positioned to define a second discrete chamber or compartment means for natural scent-source material storage.

These panel means are structured so as to permit their repositioning to enable the user to charge or recharge the respective chambers or compartments with any of various natural scent-course materials indigenous to a prospective hunting environment. These materials are scent-sources from which appropriate, natural odors will be transferred to hunters' clothing and gear.

For example, the chambers or compartments can be filled with pinecones that are often covered by potent odor-emitting pitch. Alternatively or concurrently the natural scent-source material may include hay or fruit parts that the intended quarry may sense as food. Or the material may be any of a variety of mixtures of these or other natural scent sources. Usually, however, the selected scent-source materials are environmentally hunt-specific, as determined by the skilled huntsman. That is, the materials will be selected as indigenous to the hunt region and consistent with scent expectations of the wild animal quarry.

The structure of the container means, while described as a simple box-like structure with a hinged lid, could in fact take any of a variety of forms or configurations. For example, the box-like structure need not be square or rectangular as might be expected, but could be round or otherwise curved in shape. The lid could be a mere fitted cap as opposed to a hinged arrangement, and need not be at the top of the container. Instead, a side-opening door might be provided for access to the container's inner space.

The interior panel means configured to retain and position the scent source material could be of any suitable form and may be singular or multiple in number. They could be rectangular, hinged elements as illustrated herein, or may take alternate shapes and forms. The panel means and associated elements may be constructed from diverse parts or be unitary in design. They may be fashioned of wood framing, as suggested in the accompanying illustrations, or may be of other materials as appropriate and as well known by craftsmen or skilled artisans.

The panel means are described as including wire or wire-like mesh materials, but any one of an array of possible media could be used. For example, a simple wooden panel with multiple holes drilled or otherwise formed therein could be employed. Also, rather than wire or wire-like mesh, a different meshed or woven, or even non-woven, material could be deployed utilizing natural fibers or narrow wooden strips as in an open basket weave design. All these fabrication options are seen as well within the purview and choice of the skilled artisan.

Plastic, if totally odor-free, may be substituted for any or every part of the panels, and textile fabric bags can be used as well, either with or without a mesh arrangement, but permitting scent-laden air to circulate from the scent-source material to the articles of clothing. It is important that any material used not be of a type that would impart or convey unnatural or human-associated odors to the clothing being conditioned. Again, these are matters of choice left to those skilled in the art.

When planning a hunt, the hunter's clothing is prepared as by washing, preferably in a scent-free detergent or soap, and placed in the container means for conditioning. Depending upon where the hunt will take place, natural material collected from the hunt site (or a site that would be presumed to be similar to the hunt site) will have been gathered and placed in the chamber or compartment means as natural scent-source materials.

The container means is then closed and the natural transfer of scent is permitted to occur over a period of time. Longer exposure to the scent will, to a certain extent, ensure more conditioning of the hunter's clothing and associated gear by the selected scent-source.

When readying for the hunt, the clothing may be removed from the container means and immediately worn by the hunter. Alternatively, and in some cases preferably, the entire container means can be carried as luggage to the general location of the hunt site. The latter method will avoid additional scents picked up by the clothing and gear during transport, such as fast-food grease, coffee odors, auto interior odors, exhaust emission fumes, oil or gasoline traces, cigarette, cigar or pipe smoke.

When utilized properly, this invention will greatly enhance the hunter's probability of a successful hunt, since the possibility of human associated scent detection by the quarry will be minimized.

BRIEF DESCRIPTION OF THE DRAWINGS

The invention will be more fully understood with reference to the following illustrations describing a preferred embodiment.

DETAILED DESCRIPTION

Figure 1:
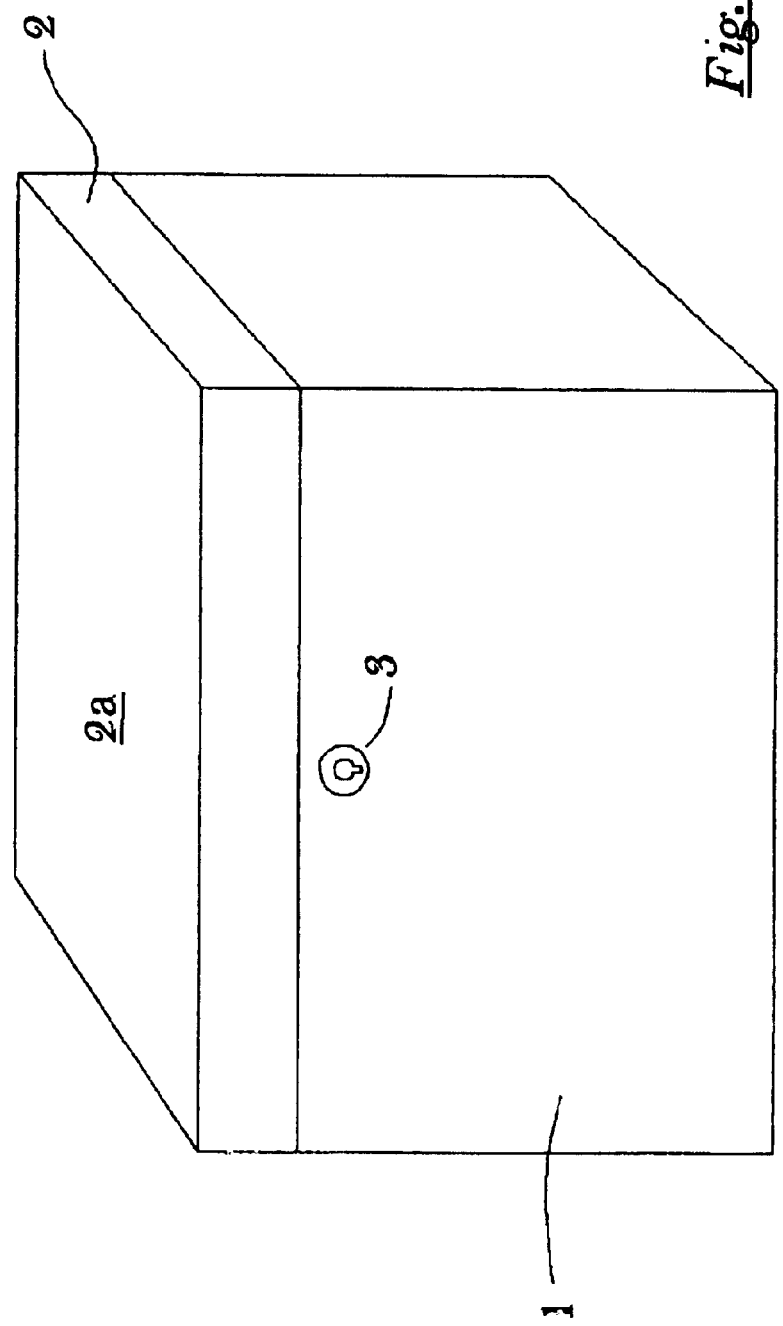
FIG. 1 is a perspective view of the device of the invention, with the container in its closed position.

Referring to the drawings, where like numerals refer to like matter throughout, and more particularly to FIG. 1, a box-like container means 1 is shown as having a lid 2 having a top 2a. The container means further includes side walls 1a, 1b, 1c, and 1d. The box-like container means, referred to herein as the HUNTER'S TRUNK™, may be provided with a keyhole 3 as part of an optional key and lock arrangement.

The container means may also have applied thereto aesthetic decorations such as hand-painted designs or decals (not shown) portraying hunting scenes, forest venues or big game images.

The container means, with the exception of typically metal lock and hinge parts, is constructed of a natural material such as wood, as would be appropriate for a storage chest for clothing and blankets.

Figure 2:
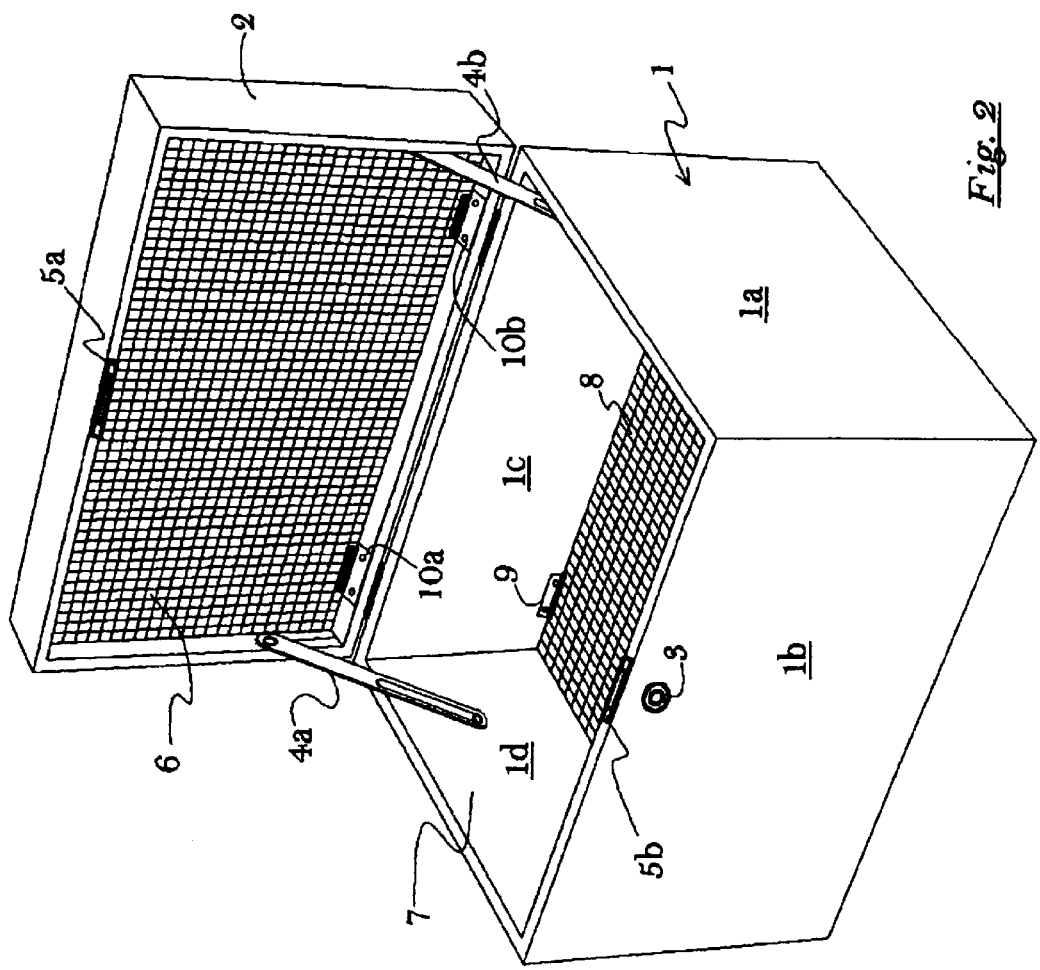
FIG. 2 is a perspective view of the device of the invention, shown in its fully open position.

In FIG. 2, the container means is illustrated in its open position where the lid 2 is raised to the full extent permissible by laterally placed adjustable straps 4a and 4b. Of course, such straps are optional, and could be singularly applied, omitted, or replaced by other lid limiting elements as desired. For example, leather strips, link chains, or rope segments could be readily substituted. Elements 5a and 5b are additional portions of the optional locking arrangement discussed hereabove and as are well known in the art.

Within the confines of lid 2 is positioned a compartment defining panel means 6 bounded at its inwardly facing surface (that is, inwardly of the container's inner space generally referenced as 7) by a mesh-like means permitting conditioning scents to waft as scent-laden air from the natural scent-source materials.

On the side of the mesh-like means opposite its inwardly facing surface, is a first compartment means (to be further discussed below) for temporary placement and storage of natural scent-source materials for the purpose of impregnating or otherwise covering and camouflaging hunter's clothing and associated hunting gear placed in the inner space 7. Compartment defining panel means 6 is conveniently hinged at 10a and 10b, as will be further discussed hereafter. Panel means 6 serves to separate first compartment means from the portion of the inner space 7 where clothing articles are to be positioned for conditioning, thus to prevent soiling of the articles by the natural scent-source materials.

Near the bottom-most area of the inner space 7, yet positioned at a point above said bottom of the container means, is shown a second compartment defining panel means 8. Said panel means 8 also includes a frame structure 8a with an inwardly facing surface defined by a mesh-like means permitting passage of scent-laden air from natural scent-source materials enclosed therein, and thus serving to facilitate the scent contact and transference to clothing articles placed within inner space 7 for conditioning.

Compartment defining panel means 8 is conveniently hinged at 9 and also hinged at a second point (not shown) on a common axis with hinge 9 and spaced laterally therefrom for proper support as would be expected in such a structural arrangement. Panel means 8 serves to separate the second compartment means from the portion of inner space 7 where clothing articles are to be positioned for conditioning, thus to prevent soiling of the articles by the natural scent-source materials.

It is noted that other equivalent means can be employed for adjustably securing such compartment defining panel means or for making such panel means removable. For example, one might employ threaded or non-threaded fasteners, hook and eye elements, brackets or shelf guides, tabs or strips, or a simple force-fit arrangement.

Figure 3:
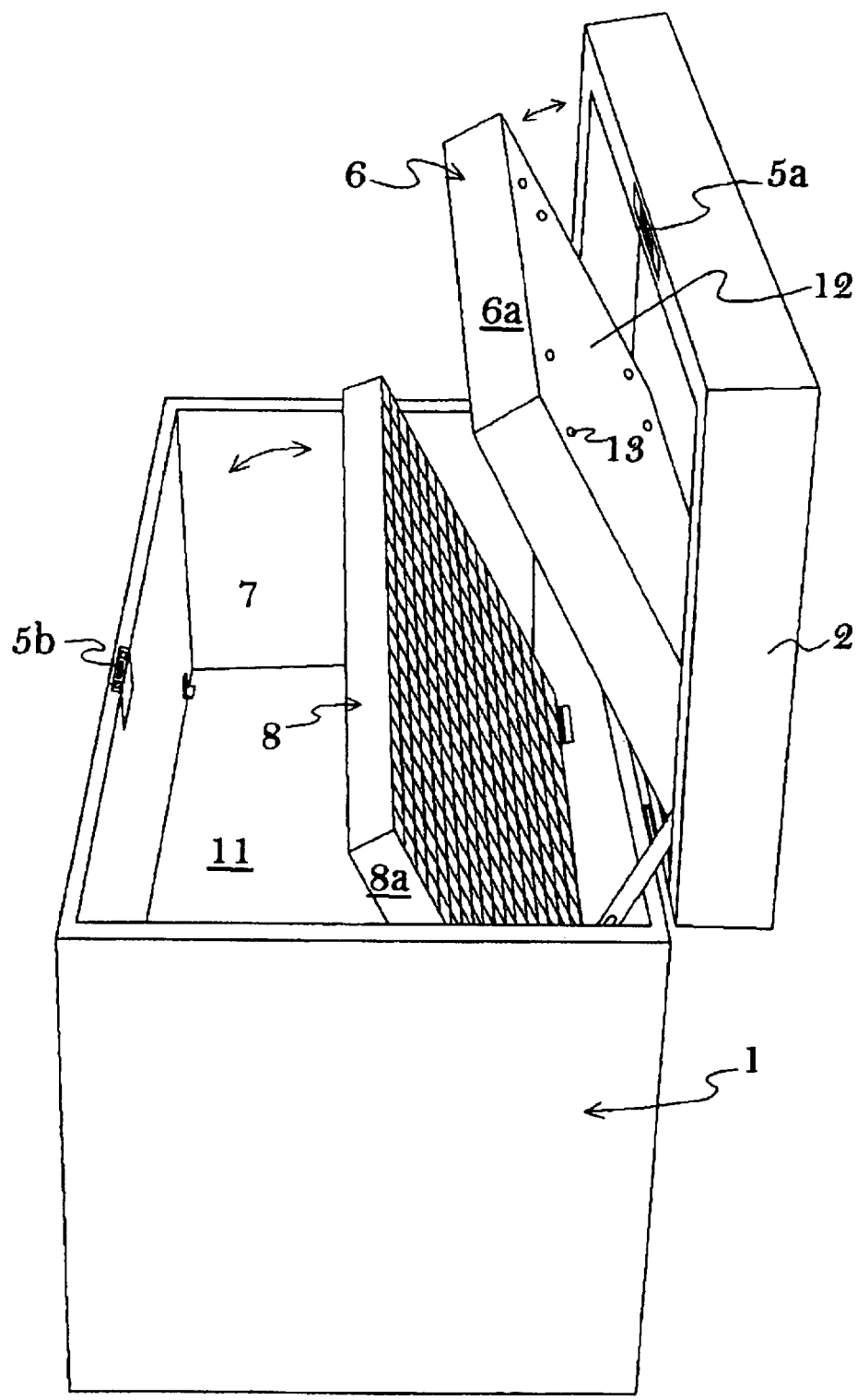
FIG. 3 is a perspective view of the device of the invention, illustrating the moveable aspects of certain interior features.

In FIG. 3, the compartment defining panel means 6 and 8 are shown in a second position swung away from their normal resting, or first positions. This view reveals a closure means 12 attached by removable fasteners 13 to the side of the panel means closest to the interior of the lid 2 for the purpose of retaining the scent-source material in place when the lid 2 is raised.

Thus, in the case of compartment defining panel means 6, the compartment means is moveable along with the panel means between a first and second position. This arrangement facilitates placement of clothing articles and gear to be conditioned, and installation of the materials that will serve as a natural scent-source.

The mesh-like nature of the inwardly facing surfaces of panel means 6 and 8 is such that the transference of odors is permitted to take place from natural scent-source materials to the hunter's clothing and gear. At the same time, the panel means prevents any incidental transference to the clothing articles and gear of contamination or soiling stains from the natural material such as sticky pine pitch. As discussed above, the mesh-like structure as well as all other elements shown may have substituted therefor any of a variety of suitable equivalents.

USE OF THE INVENTION

In anticipation of a hunting excursion, natural scent-source materials are gathered or accumulated from the hunt site or from environments typical of the hunt region (preferably during a previous hunt or site visit). These natural scent-source materials are placed in the container means 1, more particularly within the compartments defined by panel means 6 and 8. These materials will serve as the scent source that will bring about a conditioning of the clothing and gear to be employed during the hunt.

The hunter's clothing is prepared, laundered or otherwise freshened and cleaned. In doing so, care is taken to avoid the addition or accumulation of unwanted odors from soaps and detergents, fabric softeners, and ironing smells. Additionally, care is taken to resist contact of the hunter's clothing articles with other items of clothing which may be contaminated with perfumes or other artificial scents, lotion covered hands and so on, and resisting contact with other items of clothing including perfumes or artificial scents, lotion covered hands and so on.

The hunter's clothing is then placed in the container means 1, in those areas confined by the scent-source material loaded compartment means defined by panel means 6 and 8. The movement of the panel means 6 and 8 at their respective hinge points shown at 9, 10a and 10b facilitates the placement of the clothing in the spaces provided. The hinged placement of said panel means further facilitates freshening of the scent-source materials from time to time, as well.

In addition to the hunter's clothing, other hunt-related gear may be placed in the container means 1, as space permits. For example, fabric-coated canteens, belts, ammunition holders, hunting license portfolios, hats, mufflers, underclothes, side arms, gloves, boots, maps and map cases, and camping items can be placed therein for conditioning as well.

On or near the day of the hunting excursion, the clothes and gear are removed from the container means 1 and worn to the hunt. Alternatively, the clothes and gear may remain in the container while transported to the site as discussed hereabove.

More than one such container to be marketed, for example, under the namne HUNTER's TRUNK™, may be employed and displayed, affording additional family members the advantages of this clothing conditioning invention. Multiple container means 1 may in fact be designed so as to nest, one on top of the other (though not shown as such), or to be engaged in side by side configuration (also not shown).

The visual effect of a single container means as a home interior design feature is that of a handsome piece of furniture, not unlike storage trunks typically used for linens and blankets. This will be viewed as far more esthetically appealing than the thin plastic bag, meant for trash and refuse storage, but often used by hunters, and will provide far greater results in terms of odor camouflage.

The container means 1 can have a secondary use as a seat, suitably furnished with a cushion (not shown). Placed side by side, the storage and conditioning containers have the appearance and dual application of a bench for extra seating. Stacked vertically the container means 1 can be made to appear as a tall chest.

Thus the advantage of this invention are not only seen in the effective camouflaging of the hunter's clothing and gear from detection by big game with keen senses, but also in the provision of an attractive and functional piece of furniture.

Upon review of the foregoing specification and drawings, it will be evident that the method and apparatus presented are susceptible of many modifications, combinations and alterations which may differ from those set forth. The arrangements disclosed are illustrative only and not limiting as to the scope of the invention which is to be given the full breadth of any claims appended hereto and any and all equivalent thereof.

What is claimed is:

1. A device for conditioning articles of clothing including a container means,
   said container means including a top and bottom, and at least four sides cooperating to define an inner space,
   said inner space including at least one clothing storage area for receiving articles of clothing to be conditioned, said inner space further including at least one moveable compartment means for the temporary placement of natural scent-source materials,
   at least one panel means serving to separate said at least one moveable compartment means from said at least one clothing storage area, said at least one panel means further provided with passage means permitting natural and unforced circulation of scent-laden air to said at least one clothing article storage area,
   means for closing said container means to permit conditioning to take place, whereby said compartment means is moveable to facilitate the placement of scent-source materials and clothing to be conditioned, said means for closing said container means is a lid,
   said container means includes an upper-most area and bottom-most area, said at least one panel means is positioned adjacent to said bottom-most area, but spaced from said bottom to thus define said at least one compartment means, so as to support said articles while separating said articles from said natural scent-source materials.

2. The device in claim 1 wherein said at least one panel means is supported for adjustment, so as to be moved adjacent and apart from said natural scent-source materials, permitting access to said scent-source materials.

3. The device of claim 1 wherein said at least one panel means includes a frame structure to which a wire-like mesh is attached, thus forming said passage means for scent-laden air.

4. The device in claim 1 wherein said means for closing said container means is a lid,
   said container means includes an upper-most area and bottom-most area, said at least one panel means is positioned adjacent to said upper-most area to thus define said at least one compartment means, so as to support said natural scent-source materials in a position separated from said articles of clothing.

5. The device of claim 4 wherein said at least one panel means fits within said lid, and is fastened thereto,
   said one panel means includes a frame structure to which a wire-like mesh is attached, thus forming said passage means for scent-laden air.

6. The device of claim 5 wherein said frame structure further includes a closure means temporarily affixed thereto,
   said closure means is located on a side thereof remote from said inner space and adjacent an inner surface of the lid,
   said closure means holding said natural scent-source materials in place as said lid is moved to an open position.

7. The device of claim 6 wherein said one panel means is supported for adjustment, so as to be moved to positions adjacent and apart from said lid, permitting access to said scented materials through said closure means.

8. A device for conditioning articles of clothing including a container means, said container means including a top and bottom, and at least four sides cooperating to define an inner space, said top includes a lid for closing said container means to permit conditioning to take place, said inner space of said container means further including an upper-most area and bottom-most area, and at least one clothing storage area for receiving articles of clothing to be conditioned, first panel means positioned adjacent to said bottom-most area, for supporting thereon the clothing to be conditioned, said first panel means spaced from said bottom and defining therewith at least one compartment means for temporary storage of natural scent-source materials near but out of contact with said clothing articles, said first panel means further provided with passage means permitting natural and unforced circulation of scent-laden air to said at least one clothing article storage area, a second panel means positioned adjacent to said upper-most area to thus define a second compartment means for storage and support of natural scent-source materials in a position near to but separated from said articles of clothing, said second panel means provided with passage means permitting natural and unforced circulation of scent-laden air to said at least one clothing article storage area, said first and second panel means are adjustable so as to facilitate the insertion of clothing articles to be conditioned, and to provide access to the first and second compartments, said container means, when articles of clothing to be conditioned are placed therein and said natural scent-source materials are placed within the first and second compartment means, thus serves to condition said articles of clothing to impart a camouflaging scent thereto.

9. A method of conditioning articles of hunter's clothing and gear to camouflage the scent of said clothing and gear prior to a hunt including the steps of gathering a collection of natural scent-source materials from a prospective hunt site, providing a container means with an inner space that includes a holding area for hunter's clothing articles and other gear, all of which is to be conditioned, further providing said inner space with at least one container means within said inner space for temporary storage of said natural scent-source materials, placing a panel means with passages therethrough within the space to separate the clothing article space from the scent-source material while affording unforced flow of scent-laden air from the materials to the clothing articles, placing said articles of hunter's clothing and gear near said panel means, closing said container means to allow for the conditioning to take effect, opening the container means and removing the conditioned articles of clothing, using said conditioned and scent-camouflaged hunter's clothing and gear in a hunt with the result that the quarry game cannot easily detect human-associated odors therefrom.

10. A device for conditioning articles of clothing and related gear, said device including:

a container, said container including a top and bottom, and at least one side wall defining an inner space including at least one storage area for receiving clothing and gear to be conditioned;

said container further including at least one moveable compartment within said inner space for temporary placement of scent-source materials;

said at least one moveable compartment including at least one panel serving to separate said at least one moveable compartment and any scent-source materials therein from said at least one storage area;

said at least one panel further provided with at least one passage permitting unforced circulation of scent-laden air to said at least one storage area;

means for disclosing said container to permit conditioning to take place;

whereby said compartment is movable to facilitate the placement scent-source materials within said at least one compartment and placement of articles to be conditioned within said storage area, while said at least one panel separates said articles from said materials;

wherein said means for closing said container is a lid, said container includes an upper-most area and bottom-most area, said at least one panel is positioned adjacent to said bottom-most area, but spaced from said bottom to thus define said at least one compartment; so as to support said articles while separating said articles from said scent-source materials.

11. The device of claim 10 wherein said at least one panel includes a frame structure and a mesh material, said mesh material attached to said frame structure, said mesh material thus forming said passage for scentladen air;

whereby unforced scent-laden air is permitted circulation to said storage area to condition articles placed therein.

12. The device of claim 11 wherein said mesh material is selected from the group consisting of wire material, wire-like material, natural fiber material and wooden strip material.

13. The device of claim 12 wherein said mesh material is woven.

14. The device of claim 14 wherein said mesh material is non-woven.

15. A method of conditioning articles of hunter's clothing and gear to camouflage a scent of said clothing and gear prior to a hunt, said method including the steps of:

providing a container defining an inner space that includes at least one holding area for articles of hunter's clothing and gear, all of which are to be conditioned;

further providing said container, within said inner space, with at least one compartment for temporary storage of natural scent-source materials;

providing at least one moveable panel with airflow passages therethrough within said inner space to close said at least one compartment, thereby separating said at least one compartment from said at least one holding area while permitting airflow between said compartment and said holding area;

moving said at least one panel to a first position affording access to said at least one compartment and to said at least one holding area;

charging said at least one compartment with a collection of natural scent-source materials gathered from a prospective hunt site;

placing articles of hunter's clothing and gear within said at least one holding area;

moving said at least one panel to a second position wherein said scent-source materials are positioned adjacent said articles yet separated therefrom by said at least one moveable panel;

closing said container to permit conditioning of said hunter's clothing and related gear;

removing said hunter's clothing and related gear from said holding area following said conditioning;

whereby said clothing and gear are conditioned for a hunt by scents gathered from a prospective hunt site, such that quarry game cannot easily detect human-associated odors therefrom.

16. The method of conditioning articles of hunter's clothing and gear to camouflage a scent of said clothing and gear prior to a hunt, as set forth in claim 15, and further including:

providing said container, within said inner space, with at least one additional compartment for temporary storage of natural scent-source materials wherein said holding area is defined between said at least one compartment and said at least one additional compartment;

charging said at least one additional compartment with a collection of natural scent-source materials gathered from a prospective hunt site.

17. A device for conditioning articles of clothing including a container means, said container means including a top and bottom, and at least four sides cooperating to define an inner space, said inner space including at least one clothing storage area for receiving articles of clothing to be conditioned, said inner space further including at least one compartment means for the temporary placement of natural scent-source materials, at least one panel means serving to separate said at least one compartment means from said at least one clothing storage area, said at least one panel means further provided with passage means permitting natural and unforced circulation of scent-laden air to said at least one clothing article storage area, means for closing said container means to permit conditioning to take place; said means for closing said container means is a lid, said container means includes an upper-most area and bottom-most area, said at least one panel means is positioned adjacent to said bottom-most area, but spaced from said bottom to thus define said at least one compartment means, so as to support said articles while separating said articles from said natural scent-source materials.

18. The device in claim 17 wherein said at least one panel means is supported for adjustment, so as to be moved adjacent and apart from said natural scent-source materials, permitting access to said scent-source materials.

19. A device for conditioning articles of clothing including a container means, said container means including a top and bottom, and at least four sides cooperating to define an inner space, said inner space including at least one clothing storage area for receiving articles of clothing to be conditioned, said inner space further including at least one compartment means for the temporary placement of natural scent-source materials, at least one panel means serving to separate said at least one compartment means from said at least one clothing storage area, said at least one panel means further provided with passage means permitting natural and unforced circulation of scent-laden air to said at least one clothing article storage area, means for closing said container means to permit conditioning to take place; wherein said means for closing said container means is a lid;

said container means includes an upper-most area and bottom-most area, said at least one panel means is positioned adjacent to said bottom-most area, but spaced from said bottom to thus define said at least one compartment means, so as to support said articles while separating said articles from said natural scent-source materials;

wherein said at least one panel means includes a frame structure to which a mesh is attached, thus forming said passage means for scent-laden air.

20. A device for conditioning articles of clothing including a container means, said container means including a top and bottom, and at least four sides cooperating to define an inner space, said inner space including at least one clothing storage area for receiving articles of clothing to be conditioned, said inner space further including at least one compartment means for the temporary placement of natural scent-source materials, at least one panel means serving to separate said at least one compartment means from said at least one clothing storage area, said at least one panel means further provided with passage means permitting natural and unforced circulation of scent-laden air to said at least one clothing article storage area, means for closing said container means to permit conditioning to take place, wherein said means for closing said container means is a lid;

said container means includes an upper-most area and bottom-most area, said at least one panel means is positioned adjacent to said upper-most area to thus define said at least one compartment means, so as to support said natural scent-source materials in a position separated from said articles of clothing;

wherein said at least one panel means fits within said lid, and is fastened thereto, said at least one panel means includes a frame structure to which a mesh is attached, thus forming said passage means for scent-laden air.

21. The device of claim 20 wherein said frame structure further includes a closure means temporarily affixed thereto, said closure means is located on a side thereof remote from said inner space and adjacent an inner surface of the lid, said closure means holding said natural scent-source materials in place as said lid is moved to an open position.

22. The device of claim 21 wherein said at least one panel means is supported for adjustment, so as to be moved to positions adjacent and apart from said lid, permitting access to said scented materials through said closure means.

* * * * *